United States Patent [19]

Lantzsch et al.

[11] 4,078,008

[45] Mar. 7, 1978

[54] PROCESS FOR THE PREPARATION OF DIENES

[75] Inventors: Reinhard Lantzsch; Dieter Arlt, both of Cologne; Ernst Kysela, Bensberg, all of Germany

[73] Assignee: Bayer Aktiengesellschaft, Leverkusen, Germany

[21] Appl. No.: 707,783

[22] Filed: Jul. 22, 1976

[30] Foreign Application Priority Data

Aug. 16, 1975 Germany .............................. 2536504

[51] Int. Cl.$^2$ ...................... C07C 17/34; C07C 21/04; C07C 21/14; C07C 21/18
[52] U.S. Cl. ................................ 260/655; 260/653.5; 260/654 D; 260/654 R
[58] Field of Search ................. 260/655, 653.5, 654 D, 260/654 R

[56] References Cited

U.S. PATENT DOCUMENTS

| | | | |
|---|---|---|---|
| 2,581,925 | 1/1952 | Crane et al. | 260/655 |
| 2,879,311 | 3/1959 | Hawkins | 260/655 |
| 2,926,205 | 2/1960 | Bellringer | 260/655 |
| 4,018,838 | 4/1977 | Cleare | 260/654 D |

FOREIGN PATENT DOCUMENTS

| | | | |
|---|---|---|---|
| 42-11041 | 6/1965 | Japan | 260/655 |

OTHER PUBLICATIONS

Buehler et al., *Survey of Organic Synthesis*; 1970 by John Wiley and Sons, Inc.; pp. 71-72, 75-77.

*Primary Examiner*—Delbert E. Gantz
*Assistant Examiner*—J. Thierstein
*Attorney, Agent, or Firm*—Burgess, Dinklage & Sprung

[57] ABSTRACT

A process for the preparation of a diene of the formula $$\begin{array}{c} X \\ \diagdown \\ \diagup \\ Y \end{array} C=CH-CH=\overset{CH_3}{\underset{|}{C}}-CH_3 \quad (I)$$

in which

X and Y are independently fluorine, chlorine or bromine which comprises contacting a 1,1,1-trihalo-4-methyl-4-hydroxypentane of the formula $$H_3C-\underset{\underset{OH}{|}}{\overset{\overset{CH_3}{|}}{C}}-CH_2-CH_2-\underset{\underset{Z}{|}}{\overset{\overset{X}{|}}{C}}-Y \quad (II)$$

in which

X and Y have the previously assigned significance and Z is a chorine or bromine atom with a dehydrohalogenating agent and a dehydration agent.

23 Claims, No Drawings

PROCESS FOR THE PREPARATION OF DIENES

The invention relates to a new process for the preparation of dienes of the formula

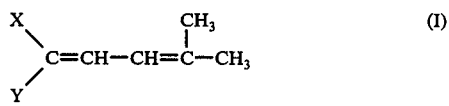

in which

X and Y independently of one another represent a fluorine, bromine or, preferably, a chlorine atom.

Processes for the preparation of dienes of the formula I are already known. However, these processes are not suitable for preparation of the compounds on an industrial scale because they are too involved; for example they require the use of magnesium-organic compounds; they are also unsuitable because large amounts of aluminum salts and zinc salts are obtained and the yields are inadequate [Bull. Soc. Chim. France 1956, 1441 and Coll. Czech. Chem. Comm. 24, 2230 (1959)].

SUMMARY OF THE INVENTION

Broadly, this invention contemplates a process for the preparation of a diene of the formula

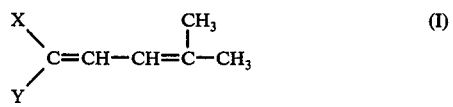

wherein

X and Y are independently fluorine, chlorine or bromine which comprises contacting a 1,1,1-trihalo-4-methyl-4-hydroxypentane of the formula

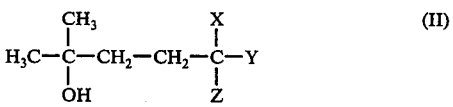

wherein

X and Y are previously assigned significance and Z is a chlorine or bromine atom with a dehydrohalogenation agent and a dehydration agent. The invention particularly contemplates the sequential dehydrohalogenation and dehydration of a 1,1,1-trihalo-4-methyl-4-hydroxypentane to obtain the desired diene of formula (I) set forth above.

It has now been found that the dienes of the formula I can be obtained in a simple reaction, which can be carried out on an industrial scale, and in good yields by the elimination of hydrogen halide and water from 1,1,1-trihalogeno-4-methyl-4-hydroxy-pentanes of the formula

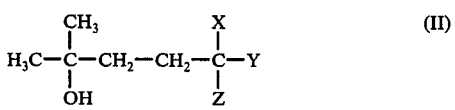

in which

X and Y have the meaning indicated under formula I and Z represents a bromine or, preferably, chlorine atom.

The invention therefore relates to a process for the preparation of dienes of the formula I, which is characterised in that hydrogen halide and water are eliminated from 1,1,1-trihalogeno-4-methyl-4-hydroxy-pentanes of the formula II.

The sequence in which the elimination of the hydrogen halide and water is carried out is arbitrary one can first split off the hydrogen halide and then dehydrate the resulting 1,1-dihalogeno-4-methyl-4-hydroxy-pentene. However, one can proceed in the converse manner and first dehydrate the 1,1,1-trihalogeno-4-methyl-4-hydroxy-pentanes of the formula II and then split off the hydrogen halide from the resulting trihalogeno-4-methyl-pent-3-enes. Preferably, the sequence dehydrohalogenationdehydration is employed.

It has proved suitable to carry out the elimination of the hydrogen halide in the presence of agents which promote the elimination of the hydrogen halide. Dehydrohalogenating agents which can be used are both basic acid-binding agents and acid dehydrohalogenation catalysts; preferably, basic acid-binding agents are used. Acid-binding agents which may be mentioned are, above all, alkali metal alcoholates, such as sodium methylate, sodium ethylate or potassium tert.-butylate, and especially alkali metal hydroxides, such as sodium hydroxide and potassium hydroxide.

Acid dehydrohalogenating agents which can be used are, for example, the salts of metals of the second and third main group and of the second and eighth sub-group of the periodic table, such as calcium chloride, barium chloride, zinc chloride, aluminum chloride and iron-III chloride.

The acid dehydrohalogenating agents are employed in amounts of 0.5–100 percent by weight, preferably 1–25 percent by weight, and the basic dehydrohalogenating agents are employed in approximately equimolar amounts, based on the compound to be dehydrohalogenated.

Elimination of the hydrogen halide is carried out at elevated temperatures. The reaction temperature depends on the dehydrohalogenating agent used; it is about 50°–150° C when basic acid-binding agents are used and between 50° and 300° C, preferably 80° and 150° C, when acid dehydrohalogenating agents are used.

It has proved advantageous to carry out the elimination of the hydrogen halide in a solvent. Examples of solvents which can be used are: alcohols, such as methanol, ethanol, propanol and isopropanol, glycol, diethylene glycol, triethylene glycol, glycol monomethyl ether and glycol monoethyl ether; methanol has proved particularly useful. The alcohols can optionally also contain water.

The elimination of the hydrogen halide can be carried out under normal pressure, but also under a slightly reduced pressure, in order to remove the hydrogen halide from the reaction mixture.

The fact that the elimination of the hydrogen halide proceeds in the presence of the basic acid-binding agents is surprising since it is known that trichloromethyl groups are converted by alkali metal hydroxides into the alkali metal salts of carboxylic acids and that an elimination of hydrogen chloride to give the dichloroolefin succeeds only in exceptional cases, for example when the carbon atom adjacent to the $CCl_3$ group is substituted by 2 aryl radicals (see J. March, Advanced Org. Chemistry, Mc.Graw-Hill 1968, page 304).

The dehydration of the 1,1-dihalogeno-4-methyl-4-hydroxy-pent-1-enes and of the 1,1,1-trihalogeno-4-methyl-4-hydroxy-pentanes can be carried out very easily. It can be carried out both in the liquid phase and also in the gas phase. For example, it can already be achieved by simply heating the compounds to temperatures of at least 150°-170° C. However, since a dehydration to give undesirable by-products, such as 1,1-dihalogeno-4-methyl-penta-1,4-dienes and to give 1,1,1-trihalogeno-4-methyl-pent-4-enes also takes place under these conditions, the elimination of water is preferably carried out in the presence of agents which promote the elimination of water.

It has been found that when the reaction is carried out in the presence of customary dehydrating catalysts, and at the lowest reaction temperature which is possible for the particular catalyst, only the desired compounds, namely the 1,1-dihalogeno-4-methyl-penta-1,3-dienes and the 1,1,1-trihalogeno-4-methyl-pent-3-enes, are formed.

Examples of dehydration catalysts which may be mentioned are: acid salts of inorganic acids, such as potassium bisulphate or sodium bisulphate; neutral salts, such as magnesium sulphate; amine salts; iodine; inorganic acids, such as phosphoric acid; carboxylic acids, such as oxalic acid, formic acid and acetic acid; carboxylic acid anhydrides, such as acetic anhydride or phthalic anhydride; sulfonic acids, such as p-toluenesulphonic acid; metal oxides, such as aluminum oxide, zirconium-IV oxide and thorium-IV oxide; acid ion exchangers; and salts of metals of the second and third main group and of the second and eighth sub-group of the periodic table, such as calcium chloride, barium chloride, zinc chloride, aluminum chloride and iron-III chloride.

The dehydrating agents are generally employed in amounts of 0.5-100% by weight, preferably 1-25% by weight, based on the weight of the compound to be dehydrated.

Preferably, bisulphates, sulphonic acids, phosphoric acid, aluminum oxide and Friedel-Crafts compounds, such as aluminum chloride, iron-III chloride and zinc chloride, are employed.

The dehydration catalysts can also be applied to supports, such as charcoal.

The elimination of water is carried out at temperatures between 20° and 300° C, preferably between 50° and 225° C.

The dehydration can be carried out, for example, in a solvent which is suitable as an entraining agent, for example chloroform, benzene, toluene, chlorobenzene or xylene. The water formed during the reaction is then continuously distilled off from the reaction mixture with the aid of the entraining agent and, after separating off the water, the entraining agent is recycled into the reaction.

However, one can distil off the water from the reaction mixture without an entraining agent. Appropriately, the procedure is then such that the starting compound and the catalyst are initially introduced into a reaction vessel which is provided with a column and a column head or with a simple distillation bridge and the mixture is heated slowly. It is possible to work under normal pressure or also under reduced pressure. The diene formed also distils off with the water formed. At the end of the distillation, the temperature at the top rises to the boiling point of the diene.

The dehydration can be carried out both discontinuously and continuously. The water formed is separated off from the distillate, the organic phase is dried and the diene is purified by distillation.

The 1,1,1-trihalogeno-4-methyl-4-hydroxy-pentanes of the formula II, which are to be employed as starting compounds in the process according to the invention, can be obtained easily by an addition reaction of trihalogenomethanes with isoprene alcohol. 1,1,1-Trichloro-4-methyl-4-hydroxy-pentane is described, for example, in J. Org. Chem. USSR 7, 1 (1971). The compounds of the formula II in which X and Y represent fluorine and Z represents chlorine; X represents fluorine and Y and Z represent chlorine; X and Y represent chlorine and Z represents bromine; X represents chlorine and Y and Z represent bromine; X, Y and Z represent bromine; or X represents fluorine and Y and Z represent bromine can be prepared analogously. When readily volatile trihalogenomethanes are used, the addition reaction must be carried out under pressure.

The 1,1-dichloro-4-methyl-penta-(1,3)-dien can be reacted with diazoacetic-acid-ethylester to 2,2-dimethyl-3-(2',2'-dichlorovinyl)-cyclopropane-1-carbonacidethylester which can be hydrolyzed in known manner to the free acid [Coll. Czech. Chem. Comm. 24, 2230 (1959)].

These products are insecticides or intermediates for insecticides (DOS Nos. 23 26 077, 24 18 950, 24 36 178 or 24 39 17).

EXAMPLE 1 a. Dehydrohalogenation 1. 31.8 g (0.5 mol) of powdered potassium hydroxide (88% pure) are added to a solution of 102.75 g (0.5 mol) of 1,1,1-trichloro-4-methyl-4-hydroxy-pentane in 200 ml of methanol and the mixture is refluxed for 8 hours, whilst stirring. After cooling, the potassium chloride which has precipitated out is filtered off and the methanol is distilled off from the filtrate in vacuo. The residue is distilled under a water pump vacuum.

76 g (90% of theory) of 1,1-dichloro-4-methyl-4-hydroxy-pent-1-ene (boiling point$_{12}$: 79°-81° C) in the form of a pale yellowish liquid are obtained.

b. Dehydration 1. 2 g of p-toluenesulphonic acid are added to a solution of 84.5 g (0.5 mol) of 1,1-dichloro-4-methyl-4-hydroxy-pent-1-ene in 300 ml of toluene and the mixture is heated to the reflux temperature under a water separator until the calculated amount of water (9 g) has separated off. The contents of the flask are then subjected to fractional distillation under a water pump vacuum.

65 g (86% of theory) of 1,1-dichloro-4-methyl-penta-1,3-diene (boiling point$_{12}$: 56° C) are obtained.

2. 68 g of potassium bisulphate are added to 84.5 g (0.5 mol) of 1,1-dichloro-4-methyl-4-hydroxy-pent-1-ene in a reaction vessel provided with a means for distillation and the mixture is heated to 200° C, whilst stirring. Water and the reaction product distil over. The water is separated off from the distillate and, after drying with sodium sulphate, the residual organic phase is subjected to fractional distillation under a water pump vacuum.

52.5 g (69.5% of theory) of 1,1-dichloro-4-methyl-penta-1,3-diene (boiling point$_{10}$: 52°-56° C) are obtained.

3. 5 g of 85% strength phosphoric acid are added to 33.8 g (0.2 mol) of 1,1-dichloro-4-methyl-4-hydroxypent-1-ene. The mixture is heated to 150°–200° C and the water and the diene formed are distilled off continuously. The water is separated off from the distillate and, after drying with sodium sulphate, the residual organic phase is subjected to fractional distillation under a water pump vacuum.

The yield of 1,1-dichloro-4-methyl-penta-1,3-diene is 88% of theory.

4. 1 g of anhydrous iron-III chloride is added to a solution of 33.8 g (0.2 mol) of 1,1-dichloro-4-methyl-4-hydroxy-pent-1-ene in 200 ml of toluene and the mixture is heated to the reflux temperature under a water separator until the calculated amount of water has separated off. 100 ml of water are then added to the contents of the flask. The organic phase is separated off, dried with sodium sulphate and subjected to fractional distillation under a water pump vacuum.

20 g (66% of theory) of 1,1-dichloro-4-methyl-penta-1,3-diene (boiling point$_{12}$: 56°–57° C) are obtained.

EXAMPLE 2 a. 4 g of anhydrous iron-III chloride are added to a solution of 205.5 g (1 mol) of 1,1,1-trichloro-4-methyl-4-hydroxy-pentane in 600 ml of toluene and the mixture is heated to the reflux temperature under a water separator until the calculated amount of water has separated off. After cooling, 200 ml of water are added to the solution. The organic phase is separated off, dried with sodium sulphate and then distilled under a water pump vacuum. The fraction having a boiling point$_{10}$ of 62°–67° C, which is thus obtained, is fractionated again.

56 g of the starting compound and 98 g (= 73% of theory, based on converted 1,1,1-trichloro-4-methyl-4-hydroxy-pentane) of 1,1,1-trichloro-4-methyl-pent-3-ene (boiling point$_{10}$: 64°–65° C) are obtained.

b. 31.8 g (0.5 mol) of powdered potassium hydroxide (88% pure) are added gradually to a solution of 93.75 g (0.5 mol) of 1,1,1-trichloro-4-methyl-pent-3-ene in 200 ml of methanol. The reaction is exothermic. The reaction mixture is then heated to the reflux temperature for 6 hours. After cooling, the potassium chloride which has separated out is filtered off and the filtrate is freed from methanol by distillation. The residue is subjected to fractional distillation.

41 g (54.5% of theory) of 1,1-dichloro-4-methyl-penta-1,3-diene (boiling point$_{11}$: 54°–57°) are obtained.

EXAMPLE 3 a. 4 g of p-toluenesulphonic acid are added to a solution of 205.5 g (1 mol) of 1,1,1-trichloro-4-methyl-4-hydroxy-pentane in 600 ml of toluene and the mixture is heated to the reflux temperature under a water separator until the calculated amount of water (18 g) has separated off. After cooling, the solution is washed with 100 ml of 1 N sodium hydroxide solution and then with 200 ml of water. The organic phase is separated off, dried with sodium sulphate and then distilled in vacuo.

128 g (68% of theory) of 1,1,1-trichloro-4-methyl-pent-3-ene (boiling point$_{12}$: 64°–66° C) are obtained.

b. 93.75 g (0.5 mol) of 1,1,1-trichloro-4-methyl-pent-3-ene and 10 g of active charcoal containing 10% by weight of barium chloride are heated to 175° C for 3 hours. After cooling, the mixture is filtered and the filtrate is distilled in vacuo.

The yield of 1,1-dichloro-4-methyl-penta-1,3-diene is 46 g (61% of theory).

What is claimed is:

1. A process for the preparation of a diene of the formula $$\begin{array}{c} X \\ \phantom{X}\diagdown \\ \phantom{XX}C=CH-CH=\underset{\underset{\displaystyle CH_3}{|}}{\overset{\overset{\displaystyle CH_3}{|}}{C}}-CH_3 \\ \phantom{X}\diagup \\ Y \end{array} \quad (I)$$

wherein
X and Y are independently fluorine, bromine or chlorine
which comprises contacting a 1,1,1-trihalo-4-methyl-4-hydroxy-pentane of the formula $$H_3C-\underset{\underset{\displaystyle OH}{|}}{\overset{\overset{\displaystyle CH_3}{|}}{C}}-CH_2-CH_2-\underset{\underset{\displaystyle Z}{|}}{\overset{\overset{\displaystyle X}{|}}{C}}-Y \quad (II)$$

wherein
X and Y have the previously assigned significance and Z is chlorine or bromine with a dehydrohalogenation agent and a dehydration agent under respectively dehydrohalogenation and dehydration conditions.

2. A process according to claim 1 wherein said pentane is initially contracted with a dehydrohalogenation agent and following dehydrohalogenation thereof is contacted with a dehydration agent to eliminate water therefrom.

3. A process according to claim 1 wherein said pentane is initially contacted with a dehydration agent and thereafter is contacted with a dehydrohalogenation agent to eliminate hydrogen halide therefrom.

4. A process according to claim 1 wherein said dehydrohalogenation agent is a basic acid binding agent.

5. A process according to claim 4 wherein said basic acid binding agent is an alkali metal alcoholate.

6. A process according to claim 1 wherein said alkali metal alcoholate is selected from the group consisting of sodium methylate, sodium ethylate and potassium tert.-butylate.

7. A process according to claim 4 wherein the basic acid binding agent is an alkali metal hydroxide.

8. A process according to claim 1 wherein the dehydrohalogenation agent is selected from the group consisting of a salt of a metal of the Second Main Group of the Periodic Table, a salt of a metal of the Third Main Group of the Periodic Table, a salt of a metal of the Second Sub-Group of the Periodic Table and a salt of a metal of the Eighth Sub-Group of the Periodic Table.

9. A process according to claim 8 wherein said dehydrohalogenation agent is selected from the group consisting of calcium chloride, barium chloride, zinc chloride, aluminum chloride and iron-III chloride.

10. A process according to claim 1 wherein the dehydrohalogenation agent is present in the reaction mixture in an amount of 0.5–10% by weight.

11. A process according to claim 10 wherein the dehydrohalogenation agent is present in the reaction mixture in the amount of 1–25% by weight.

12. A process according to claim 10 wherein the dehydrohalogenation is effected with a basic acid binding agent at a temperature between 50° and 150° C.

13. A process according to claim 1 wherein dehydrohalogenation is effected at a temperature between 50° and 300° C employing a dehydrohalogenation agent which is a salt of a metal of the Second Main Group of the Periodic Table, a salt of a metal of the Third Main Group of the Periodic Table, a salt of a metal of the Second Sub-Group of the Periodic Table or a salt of a metal of the Eighth Sub-Group of the Periodic Table.

14. A process according to claim 1 wherein the dyhydration agent is selected from the group consisting of an acid salt of an inorganic acid, a neutral salt, an amine salt, a carboxylic acid, a carboxylic acid anhydride, iodine, an acid ion exchanger, a salt of a metal of the Second and Third Main Groups or the Second and Eighth Sub-Groups of the Periodic Table, iodine, a sulfonic acid and a metal oxide.

15. A process according to claim 14 wherein the dehydration agent is present in the reaction mixture in an amount of 0.5-100% by weight.

16. A process according to claim 14 wherein the dehydration agent is present in the reaction mixture in an amount of 1 to 25% by weight.

17. A process according to claim 14 wherein the dehydration agent is selected from the group consisting of potassium bisulfate, sodium bisulfate, magnesium sulfate, iodine, phosphoric acid, oxalic acid, formic acid, acetic acid, acetic anhydride, phthalic anhydride, p-toluene sulfonic acid, aluminum oxide, zirconium-IV oxide, thorium oxide, calcium chloride, barium chloride, zinc chloride, aluminum chloride and iron-III chloride.

18. A process according to claim 14 wherein the dehydration is effected at a temperature between 20° and 300° C.

19. A process according to claim 18 wherein the dehydration is effected at a temperature between 50° and 225° C.

20. A process according to claim 1 wherein said pentane is 1,1,1-trichloro-4-methyl-4-hydroxypentane.

21. A process according to claim 1 wherein the dehydrohalogenation agent is selected from the group consisting of the salt of a metal of the Second Main Group of the Periodic Table and a salt of a metal of Third Main Group of the Periodic Table.

22. A process according to claim 2 wherein the dehydrohalogenation agent is selected from the group consisting of a salt of a metal of the Second Main Group of the Periodic Table and a salt of a metal of the Third Main Group of the Periodic Table.

23. A process according to claim 2 wherein said dehydrohalogenation agent is selected from the group consisting of sodium methylate, sodium ethylate and potassium tert butylate.

* * * * *